(12) United States Patent
Hehrmann et al.

(10) Patent No.: US 9,744,358 B2
(45) Date of Patent: Aug. 29, 2017

(54) SYSTEM AND METHOD FOR NEURAL COCHLEA STIMULATION

(71) Applicant: Advanced Bionics AG, Stäfa (CH)

(72) Inventors: Phillipp Hehrmann, Hannover (DE); Idrick Akhoun, Hannover (DE)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 15/024,426

(22) PCT Filed: Sep. 30, 2013

(86) PCT No.: PCT/EP2013/070355
§ 371 (c)(1),
(2) Date: Mar. 24, 2016

(87) PCT Pub. No.: WO2015/043677
PCT Pub. Date: Apr. 2, 2015

(65) Prior Publication Data
US 2016/0243362 A1    Aug. 25, 2016

(51) Int. Cl.
*A61N 1/00* (2006.01)
*A61N 1/36* (2006.01)
(Continued)

(52) U.S. Cl.
CPC ....... *A61N 1/36032* (2013.01); *A61N 1/0541* (2013.01); *A61N 1/37241* (2013.01);
(Continued)

(58) Field of Classification Search
USPC .......................................................... 607/57
See application file for complete search history.

(56) References Cited

U.S. PATENT DOCUMENTS 6,219,580 B1    4/2001    Faltys et al.
6,751,505 B1    6/2004    Van Den Honert et al.
(Continued)

FOREIGN PATENT DOCUMENTS

WO    2010/150002 A1    12/2010
WO    2011/032021 A1    3/2011
WO    2012/162349 A1    11/2012

*Primary Examiner* — Nicole F Johnson
(74) *Attorney, Agent, or Firm* — ALG Intellectual Property, LLC

(57) ABSTRACT

A system having a device for neural stimulation of a patient's cochlea, an in-situ device for measuring a patient's response to the neural stimulation of the cochlea, and a programming unit for adjusting the stimulation device; the stimulation device having a stimulation signal unit for generating a stimulation signal formed of pulses having a shape determined by a shape parameter set including at least one shape parameter; a cochlear implant stimulation arrangement with a plurality of stimulation channels for stimulating the cochlea based on the stimulation signal; the measuring device providing patient-specific response data concerning the stimulation response to a programming unit that controls the stimulation signal unit by subsequently supplying a plurality of different test shape parameter sets to the stimulation signal unit for causing the stimulation signal unit to generate corresponding test pulses, the programming unit evaluating each test shape parameter set based on stimulation response data.

23 Claims, 5 Drawing Sheets

(51) Int. Cl.
*A61N 1/05* (2006.01)
*A61N 1/372* (2006.01)
*A61B 5/04* (2006.01)
*A61B 5/12* (2006.01)
*A61B 5/00* (2006.01)

(52) U.S. Cl.
CPC ............ *A61B 5/04001* (2013.01); *A61B 5/12* (2013.01); *A61B 5/4047* (2013.01)

(56) References Cited

U.S. PATENT DOCUMENTS

| | | |
|---|---|---|
| 7,206,640 B1 | 4/2007 | Overstreet |
| 7,282,877 B2 | 10/2007 | Takemasa et al. |
| 7,974,697 B2 | 7/2011 | Maschino et al. |
| 8,422,706 B2 | 4/2013 | Kulkarni et al. |
| 2007/0260292 A1* | 11/2007 | Faltys ................ A61N 1/36032 607/57 |
| 2011/0077712 A1* | 3/2011 | Killian .................... A61B 5/12 607/57 |
| 2011/0082521 A1 | 4/2011 | Botros et al. |
| 2012/0130449 A1 | 5/2012 | Carlyon et al. |
| 2013/0303941 A1* | 11/2013 | Porges .................. A61B 5/125 600/559 |

* cited by examiner

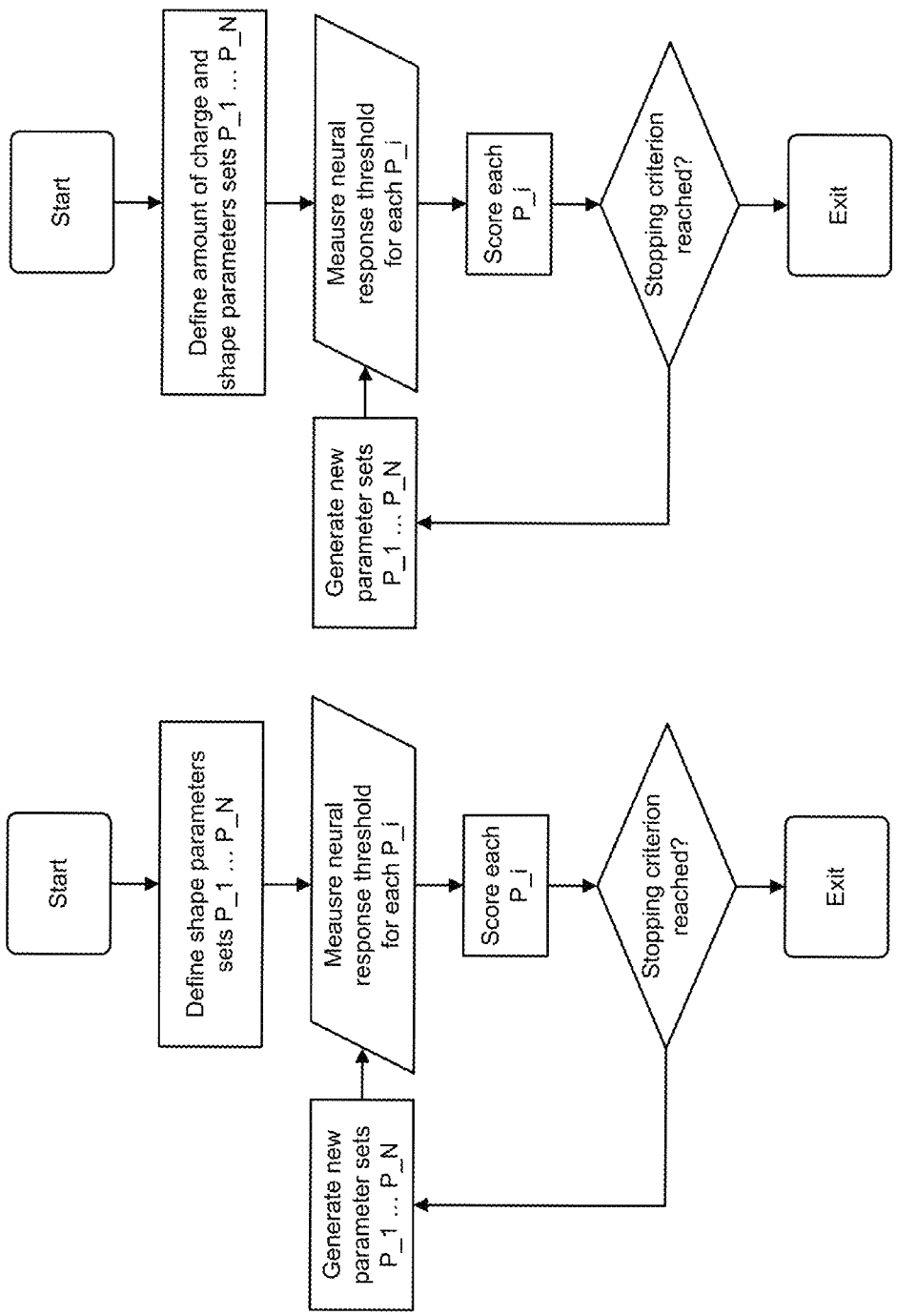

SYSTEM AND METHOD FOR NEURAL COCHLEA STIMULATION

BACKGROUND OF THE INVENTION

Field of the Invention

The invention relates to a system comprising a device for neural stimulation of a patient's cochlea and a programming unit for adjusting the stimulation device.

Description of Related Art

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence, destruction or malfunction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant (CI) systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea of a patient. The electrodes form a number of stimulation channels through which electrical stimulation pulses may be applied directly to auditory nerves within the cochlea. An audio signal may then be presented to the patient by translating the audio signal into a number of electrical stimulation pulses and applying the stimulation pulses directly to the auditory nerve within the cochlea via one or more of the electrodes.

Typically, the audio signal, which usually is captured by a microphone, is divided into a plurality of analysis channels, each containing a frequency domain signal representative of a distinct frequency portion of the audio signal, wherein the frequency domain signal in each analysis channel may undergo signal processing, such as by applying channel-specific gain to the signals. The processed frequency domain signals are used for generating certain stimulation parameters according to which the stimulation signals in each stimulation channel is generated. The analysis channels are linked to the stimulation channels via channel mapping. The number of stimulation channels may correspond to the number of analysis channels, or there may be more stimulation channels than analysis channels, or there may be more analysis channels than stimulation channels. Various stimulation strategies are used, such as current steering stimulation (in order to maximally excite a stimulation site located in between areas associated with two or more electrodes) and N-of-M stimulation (wherein stimulation current is only applied to N of M total stimulation channels during a particular stimulation frame).

An example for such a CI system with electrical cochlea stimulation is described in International Patent Application Publication WO 2011/032021 A1 and corresponding U.S. Pat. No. 8,422,706.

Typically, neural stimulation of the cochlea occurs by electric pulses applied via an electrode array implanted within the cochlea; alternatively or in addition neural stimulation of the cochlea may occur via light pulses or heat pulses applied within the cochlea.

For electric stimulation CI devices deliver trains of electrical pulses via an electrode array implanted within the cochlea which evoke neural responses in the auditory nerve. In present systems, pulse shapes are typically biphasic, with equal current amplitudes and durations of the positive and negative phase and with an optional gap in-between the two phases.

The basic functioning of the electrodes and integrity of electrode-nerve interface can be assessed by measurements of the auditory nerve response elicited by electrical stimulation. Electrically-evoked compound action potentials (ECAPs) can be recorded on the intracochlear electrodes and sent back to the implant external processor by back-telemetry. The ECAP is a voltage signal that comprises a negative and smaller positive peak; the typical order of magnitude of the ECAP is between 50 and 500 microvolts. To a first approximation, the ECAP magnitude is monotonically related to the amount of auditory nerve fibers that responded to the stimulus. Cochlear implant manufacturers have developed software tools to easily set stimulation and recording parameters and monitor the corresponding ECAP response. Examples of such neural response measurements are found in U.S. Pat. No. 7,282,877 B1. Another measure of the evoked neural activity is the auditory brain stem response (ABR) which may be recorded via external scalp electrodes.

The article "Efficiency analysis of waveform shape for electrical excitation of nerve fibers" by A. Wongsarnpigoo et al., in IEEE Trans Neural Syst Rehabil Eng 18(3), 2010, pages 319 to 328, relates to a study wherein, using a population model of mammalian axons and in vivo experiments on the cat sciatic nerve, the effects of waveform shape and duration on the charge, power and energy efficiency of neural stimulation were investigated.

U.S. Pat. No. 6,751,505 B1 relates to a CI system wherein the stimulation rate and the operation mode, including the staggering order of the pulses, are adjusted according to the neural response to the pulses which is measured in-situ by neural response telemetry utilizing the electrode array.

International Patent Application Publication WO 2010/150002 A1 and corresponding U.S. Patent Application Publication 2012/0130449 relate to a CI system wherein the wave shape of the pulses depends on the location of the electrode; it is mentioned that by varying the waveshape between its normal and inverted versions the effectiveness of the neural stimulation can be varied in location between a position close to the driven electrode and a position close to the reference electrode.

U.S. Pat. No. 6,219,580 B1 relates to a CI system comprising a pulse table for defining the stimulation pattern.

U.S. Pat. No. 7,974,697 B2 relates to an implantable neural stimulation device, wherein stimulation signal parameters are adjusted according to a brain map obtained by using a medical imaging device.

The article "Effects of waveform shape on human sensitivity to electrical stimulation of the inner ear" by A. van Wieringen et al., in Hearing Research 200 (2005), pages 73 to 86, relates to a study on how thresholds and dynamic ranges of CI users can be controlled by manipulating the way in which the charge produced by the initial phase of an electrical is recovered, wherein different types of pulses are investigated.

The article "Effect of electrical pulse shape on AVCN unit responses to cochlear stimulation" by J. A. Wiler et al., in Hearing Research 39 (1989), pages 251 to 262, relates to a study on the effect of electrical pulse shape on stimulation of guinea pig cochlea.

The article "Asymmetric pulses in cochlear implants: effects of pulse shape, polarity and rate" by O. Macherey et al., in JARO 7 (2006), pages 253 to 266 relates to a study on the perception effects of the shape, polarity and rate of asymmetric pulses.

The article "Forward-masking patterns produced by symmetric and asymmetric pulse shapes in electric hearing" by O. Macherey et al., in J. Acoust. Soc. Am. 127 (1), 2010, pages 326 to 338 relates to a study concerning forward-masking experiments with varying pulse shapes.

The article "The perceptual effects of inter phase gap duration in cochlear implant stimulation" by C. M. McKay at al., Hearing Research 181 (2003), pages 94 to 99 relates to a study on the effect of interphase gap duration on loudness perception.

SUMMARY OF THE INVENTION

It is an object of the invention to provide for a system for neural cochlear stimulation having a particularly low power consumption of the stimulation process; it is a further object to provide for a method of adjusting a device for neural cochlear stimulation.

According to the invention, these objects are achieved by a system as and a method as described herein.

The invention is beneficial in that, by applying test stimulation signals and measuring a response of the patient to the test stimulation signals in-situ, with the pulse shape parameter sets being evaluated according to the power consumption of the respective pulse and the stimulation response of the respective pulse, the pulse shape can be individually optimized with regard to power consumption and stimulation efficiency, so that the power consumption required for a given stimulation response can be minimized.

According to one embodiment, the programming unit is adapted to obtain for each shape parameter set under test an amplitude scaling factor required to evoke a predetermined response by the patient, wherein the amplitude scaling factor is used for evaluating the power consumption of the respective test pulse, i.e. that test shape parameter set is selected as the optimal test shape parameter set which results in the lowest amplitude scaling factor.

According to an alternative embodiment, the programming unit is adapted to provide the test shape parameters such that each test shape parameter set results in the same predetermined power consumption of the respective test pulse, wherein that test shape parameter set is selected as the optimal test shape parameter set which results in the largest stimulation response level.

Preferably, the patient specific response data are obtained from ECAP measurements. Preferably, the programming unit is adapted to supply and evaluate the test shape parameter sets in subsequent groups, wherein for each group the test shape parameter sets are scored, wherein the test shape parameter sets of each group are selected according to the evaluation result of the previous group of test shape parameter sets, and wherein that optimal test shape parameter set is selected for programming of the stimulation device which results in the best evaluation across all subsequent groups.

Hereinafter, examples of the invention will be described with reference to the accompanying drawings.

BRIEF DESCRIPTION OF THE DRAWINGS

FIG. 5 is a flow chart of one example of the optimization procedure of the stimulation pulse shape according to the invention;

FIG. 6 is a flow chart of an alternative example of the optimization procedure of the stimulation pulse shape according to the invention;

DETAILED DESCRIPTION OF THE INVENTION

Figure 1:
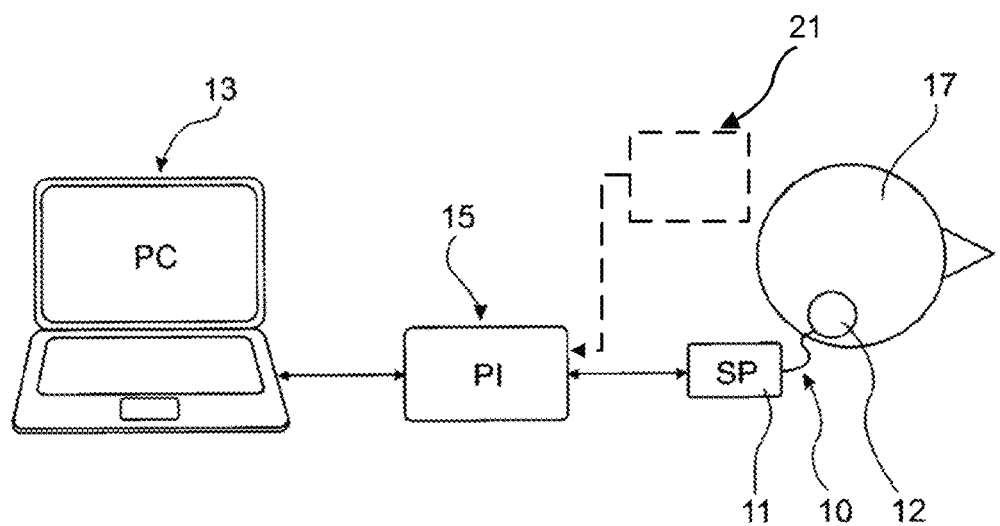
FIG. 1 is a schematic representation of an example of a system according to the invention.

FIG. 1 is a schematic representation of an example of a neural stimulation system according to the invention, comprising a programming unit 13, which may be implemented as a computer, a programming interface 15 and a CI device 10 comprising a sound processing subsystem 11 and an implantable relation subsystem 12, with the CI device being worn by a patient 17. The programming unit 13 communicates with the sound processing subsystem 11 via the programming interface 15, which may be implemented as a wired or wireless connection.

The programming unit 13 serves to control the sound processing subsystem 11 such that test stimulation signals are applied to the patient 17 via the stimulation subsystem 12 and to evaluate the test stimulation signals according to their power consumption and according to the stimulation response created by the test stimulation signals, with the stimulation response, according to a preferred embodiment, being measured by the CI device 10. According to an alternative embodiment, the stimulation response may be measured by a physiological measuring device (indicated at 21 in FIG. 1) which may be provided in addition to the CI device 10.

It is to be understood that the programming unit 13 is used with the CI device 10 only for adjustment/fitting, but not during normal operation of the CI device 10.

Figure 2:
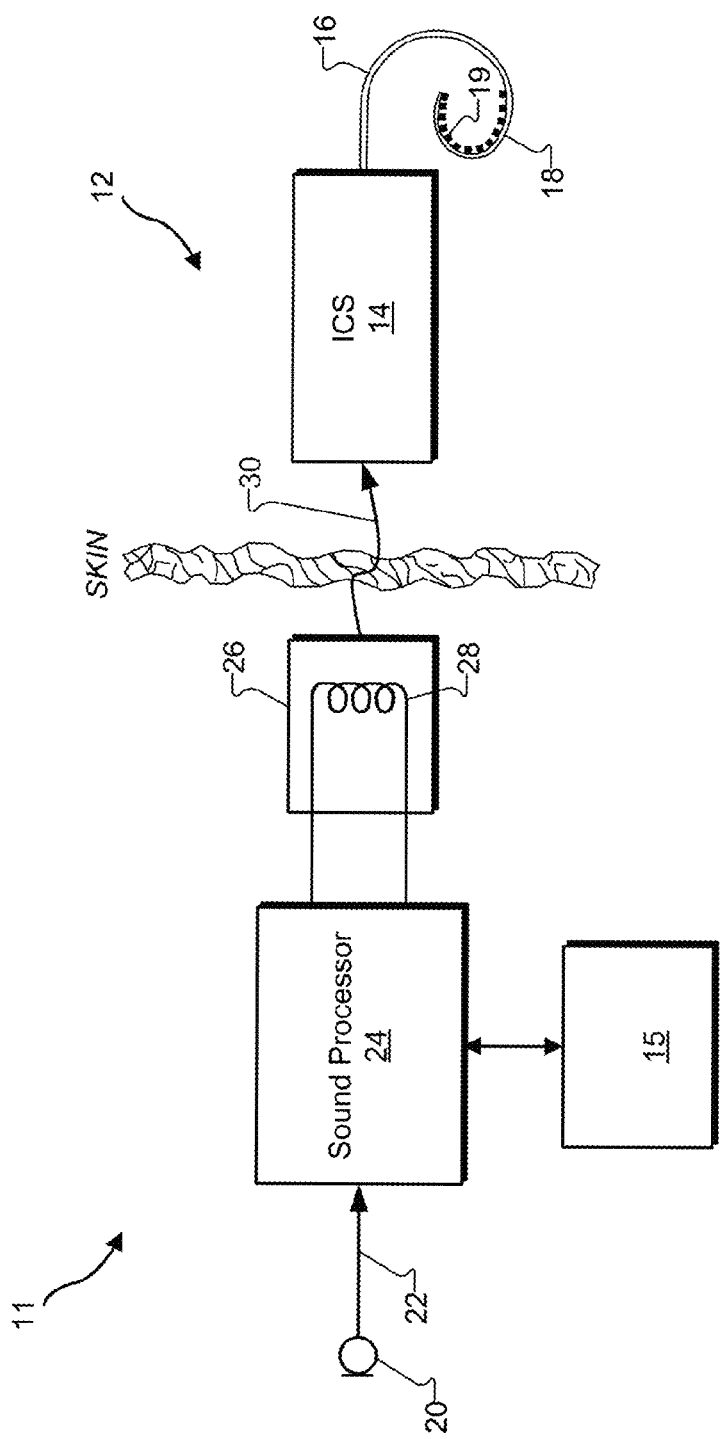
FIG. 2 is a schematic representation of an example of the CI device of the system of FIG. 1.

In FIG. 2 an example of the cochlear implant device 10 of the system of FIG. 1 is shown schematically. The sound processing sub-system 11 serves to detect or sense an audio signal and divide the audio signal into a plurality of analysis channels, each containing a frequency domain signal (or simply "signal") representative of a distinct frequency portion of the audio signal. A signal level value and a noise level value are determined for each analysis channel by analyzing the respective frequency domain signal, and a noise reduction gain parameter is determined for each analysis channel as a function of the signal level value and the noise level value of the respective analysis channel. Noise reduction is applied to the frequency domain signal according to the noise reduction gain parameters to generate a noise reduced frequency domain signal. Stimulation parameters are generated based on the noise reduced frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlear of a patient 17 in accordance with the stimulation parameters received from the sound processing sub-system 11. Electrical stimulation is provided to the patient 17 via a CI stimulation assembly 18 comprising a plurality of stimulation channels, wherein various known stimulation strategies, such as current steering stimulation or N-of-M stimulation, may be utilized. In addition, the stimulation assembly 18 also may be used for ECAP measurements via reverse telemetry, as will be described in more detail with regard to FIG. 8 below.

As used herein, a "current steering stimulation strategy" is one in which weighted stimulation current is applied concurrently to two or more electrodes by an implantable cochlear stimulator in order to stimulate a stimulation site located in between areas associated with the two or more electrodes and thereby create a perception of a frequency in between the frequencies associated with the two or more electrodes, compensate for one or more disabled electrodes, and/or generate a target pitch that is outside a range of pitches associated with an array of electrodes.

As used herein, an "N-of-M stimulation strategy" is one in which stimulation current is only applied to N of M total stimulation channels during a particular stimulation frame, where N is less than M. An N-of-M stimulation strategy may be used to prevent irrelevant information contained within an audio signal from being presented to a CI user, achieve higher stimulation rates, minimize electrode interaction, and/or for any other reason as may serve a particular application.

The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp on time, and ramp off time of the stimulation current that is applied to the stimulation site.

Figure 3:
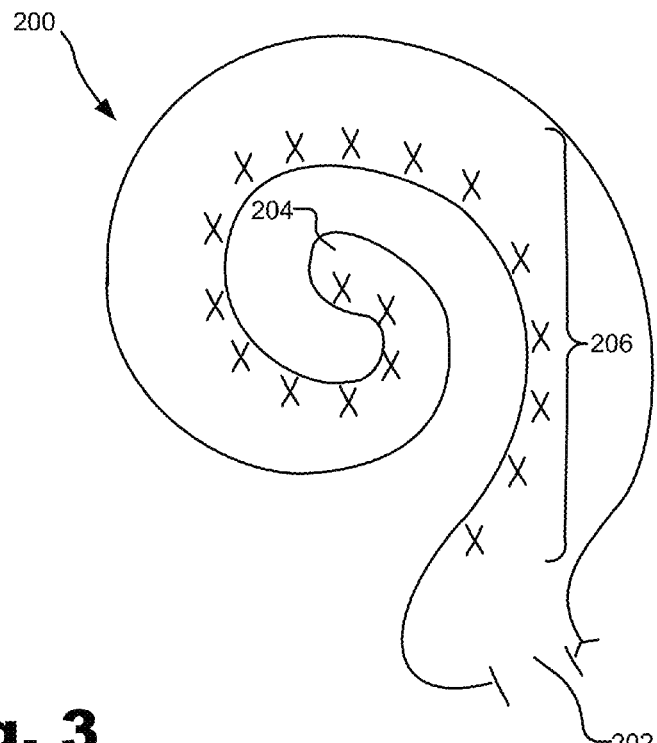
FIG. 3 is a schematic cross-sectional view of a human cochlea with marked stimulation sites.

FIG. 3 illustrates a schematic structure of the human cochlea 200. As shown in FIG. 3, the cochlea 200 is in the shape of a spiral beginning at a base 202 and ending at an apex 204. Within the cochlea 200 resides auditory nerve tissue 206 which is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 12 is configured to apply stimulation to different locations within the cochlea 200 (e.g., different locations along the auditory nerve tissue 206) to provide a sensation of hearing.

Returning to FIG. 2, sound processing subsystem 11 and stimulation subsystem 12 is configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application.

In the example shown in FIG. 2, the stimulation subsystem 12 comprises an implantable cochlear stimulator ("ICS") 14, a lead 16 and the stimulation assembly 18 disposed on the lead 16. The stimulation assembly 18 comprises a plurality of "stimulation contacts" 19 for electrical stimulation of the auditory nerve. The lead 16 may be inserted within a duct of the cochlea in such a manner that the stimulation contacts 19 are in communication with one or more stimulation sites within the cochlea, i.e. the stimulation contacts 19 are adjacent to, in the general vicinity of, in close proximity to, directly next to, or directly on the respective stimulation site.

In the example shown in FIG. 2, the sound processing sub-system 11 is designed as being located external to the patient 17; however, in alternative examples, at least one of the components of the sub-system 10 may be implantable.

In the example shown in FIG. 2, the sound processing sub-system 11 comprises a microphone 20 which captures audio signals from ambient sound, a microphone link 22, a sound processor 24 which receives audio signals from the microphone 20 via the link 22, and a headpiece 26 having a coil 28 disposed therein. The sound processor 24 is configured to process the captured audio signals in accordance with a selected sound processing strategy to generate appropriate stimulation parameters for controlling the ICS 14 and may include, or be implemented within, a behind-the-ear (BTE) unit or a portable speech processor ("PSP"). In the example of FIG. 2 the sound processor 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links. According to an alternative embodiment, the sound processor 24 and the ICS 14 may be directly connected by wires.

Figure 4:
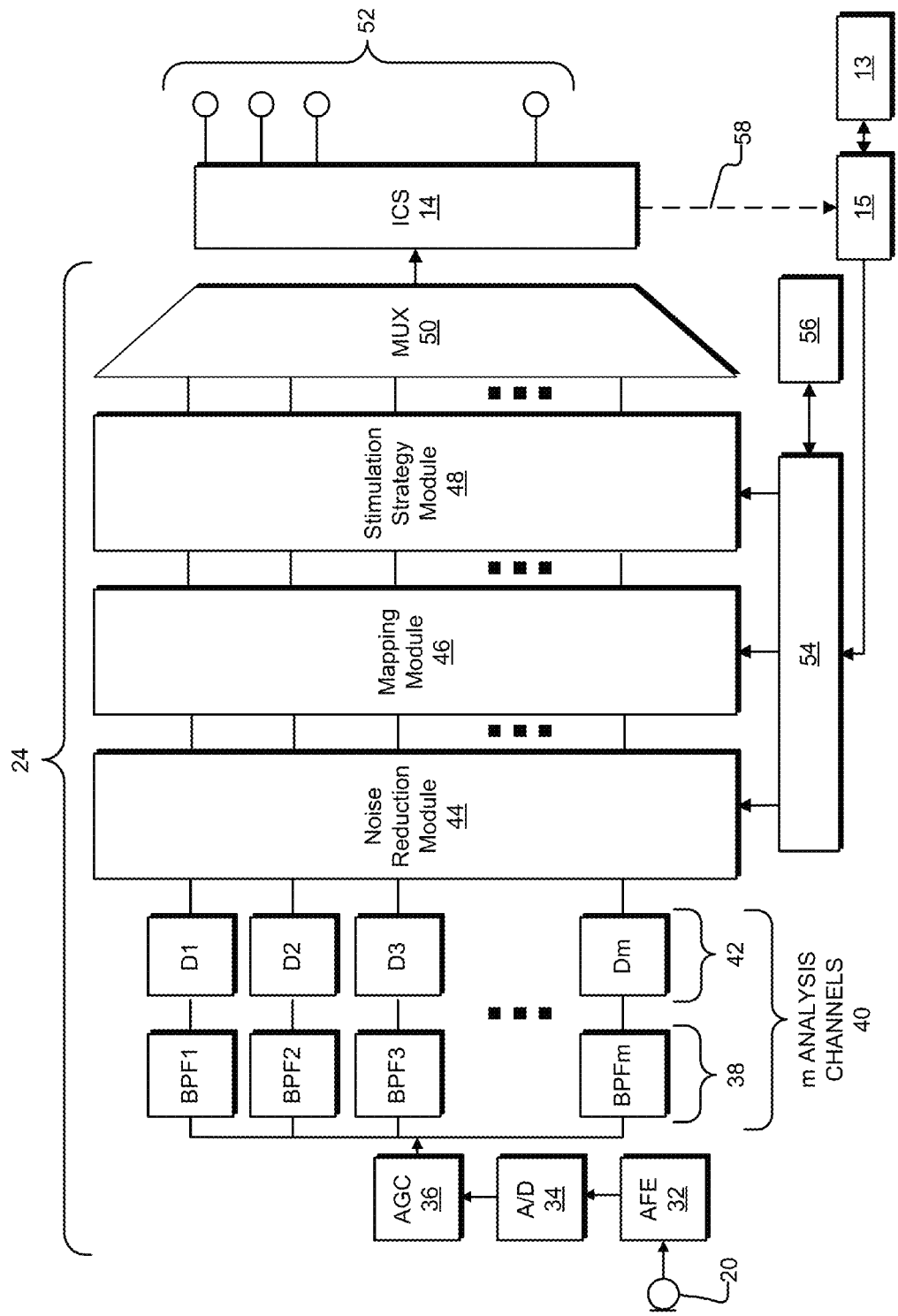
FIG. 4 is a block diagram of an example of the signal processing structure of a CI device to be used with the present invention.

In FIG. 4, a schematic example of a sound processor 24 is shown. The audio signals captured by the microphone 20 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36.

After appropriate automatic gain control, the digital signal is subjected to a filter bank 38 comprising a plurality of filters F1 . . . Fm (for example, band-pass filters) which are configured to divide the digital signal into m analysis channels 40, each containing a signal representative of a distinct frequency portion of the audio signal sensed by the microphone 20. For example, such frequency filtering may be implemented by applying a Discrete Fourier Transform to the audio signal and then divide the resulting frequency bins into the analysis channels 40.

The signals within each analysis channel 40 are input into an envelope detector 42 in order to determine the amount of energy contained within each of the signals within the analysis channels 40 and to estimate the noise within each channel. After envelope detection the signals within the analysis channels 40 are input into a noise reduction module 44, wherein the signals are treated in a manner so as to reduce noise in the signal in order to enhance, for example, the intelligibility of speech by the patient. Examples of the noise reduction module 44 are described in International Patent Application Publication WO 2011/032021 A1 and corresponding U.S. Pat. No. 8,422,706.

The noise reduced signals are supplied to a mapping module 46 which serves to map the signals in the analysis channels 40 to the stimulation channels S1 . . . Sn. For example, signal levels of the noise reduced signals may be mapped to amplitude values used to define the electrical stimulation pulses that are applied to the patient 17 by the ICS 14 via M stimulation channels 52. For example, each of the m stimulation channels 52 may be associated to one of the stimulation contacts 19 or to a group of the stimulation contacts 19.

The sound processor 24 further comprises a stimulation strategy module 48 which serves to generate one or more stimulation parameters based on the noise reduced signals and in accordance with a certain stimulation strategy (which may be selected from a plurality of stimulation strategies). For example, stimulation strategy module 48 may generate stimulation parameters which direct the ICS 14 to generate and concurrently apply weighted stimulation current via a plurality 52 of the stimulation channels S1 . . . Sn in order to effectuate a current steering stimulation strategy. Additionally or alternatively the stimulation strategy module 48 may be configured to generate stimulation parameters which direct the ICS 14 to apply electrical stimulation via only a subset N of the stimulation channels 52 in order to effectuate an N-of-M stimulation strategy.

The sound processor 24 also comprises a multiplexer 50 which serves to serialize the stimulation parameters generated by the stimulation strategy module 48 so that they can be transmitted to the ICS 14 via the communication link 30, i.e. via the coil 28.

The sound processor 24 may operate in accordance with at least one control parameter which is set by a control unit 54. Such control parameters may be the most comfortable listening current levels (MCL), also referred to as "M levels", threshold current levels (also referred to as "T levels"), dynamic range parameters, channel acoustic gain parameters, front and back end dynamic range parameters, current steering parameters, amplitude values, pulse rate values, pulse width values, polarity values and/or filter characteristics. Examples of such auditory prosthesis devices, as described so far, can be found, for example, in International Patent Application Publication WO 2011/032021 A1 and corresponding U.S. Pat. No. 8,422,706.

The stimulation strategy module 48 also controls the shape of the stimulation pulses. In general, the pulse shape is determined by a shape parameter set including at least one shape parameter. Such shape parameter set may be stored in a memory 56.

Figure 7:
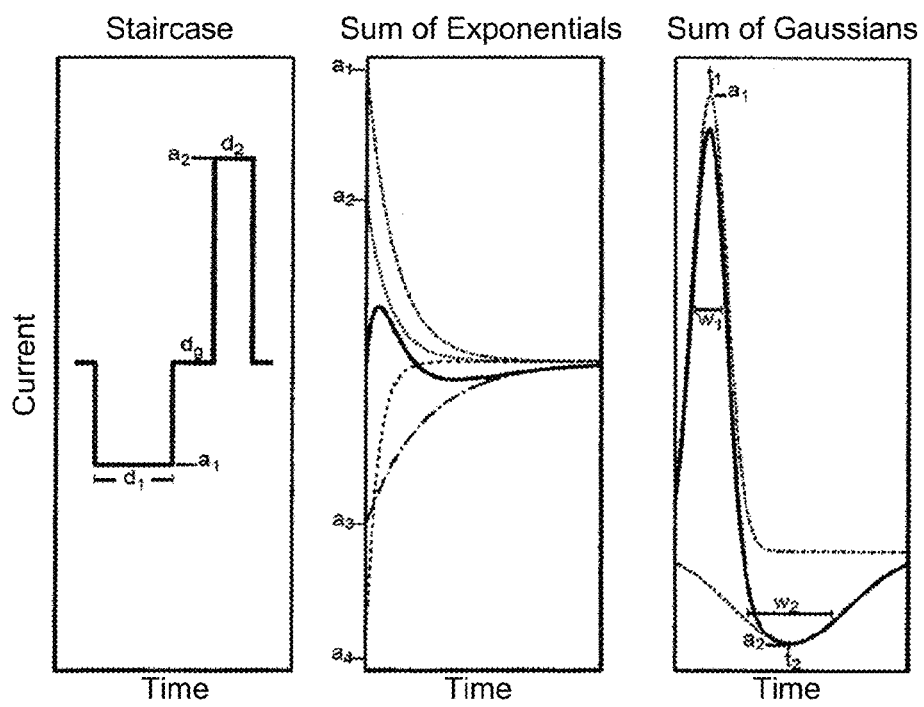
FIG. 7 shows three different types of stimulation pulse shapes which may be used with the present invention.

Examples of different types of pulse shapes are shown in FIG. 7. The left-hand example in FIG. 7 shows an asymmetric biphasic pulse which may be described, for example by the following parameters: duration of the negative phase ($d_1$), amplitude of the negative phase ($a_1$), duration of the positive phase ($d_2$), amplitude of the positive phase ($a_2$), and duration of the interphase gap ($d_g$).

While the example shown at the left-hand of FIG. 7 is a staircase pulse, other parameterizations are also conceivable. For example, the pulse shape could be described in terms of an arbitrary set of basic functions, such as a sum of exponential-shaped pulses (see center of FIG. 7, wherein the pulse is parameterized by the peak amplitudes ($a_1, a_2, a_3, a_4$) of four exponentials different fixed decay rates) or Gaussian shaped pulses (see right-hand of FIG. 7, wherein the pulse is parameterized by the peak times ($t_1, t_2$), amplitudes ($a_1, a_2$) and pulse widths ($w_1, w_2$) of two Gaussian-shaped pulses). The motivation for such different representation could be two-fold. Firstly, an appropriate set of basic functions can provide for a more parsimonious representation of complex analog or quasi-analog pulse shapes than a finely sampled staircase. Hence, the number of optimization parameters and the time required for the optimization may be reduced, even if the idealized analog shape is finally delivered approximately as a staircase pattern by the CI implant electronics (as it is presently typically the case). Secondly, more advanced CI devices may not be restricted to staircase stimulation patterns but may even use current sources which physically generate non-rectangular pulses themselves.

The programming unit 13 is connected to the CI device 10 via the programming interface 15 for programming the CI device in a manner so as to optimize the pulse shape with regard to power consumption. To this end, the programming unit 13 may communicate with the control unit 54 in order to make the CI device 10 subsequently apply test stimulation signals having pulses of different test shapes defined by a plurality of different test shape parameter sets. For example, the test shape parameter sets may implement systematic variations of the duration and amplitude of the negative and positive phase and the interphase gap duration.

Further, the programming unit 13 determines the power consumption for evaluation of the respective test pulses.

In addition, the stimulation response to each test pulse is measured and the respective stimulation response data is supplied to the programming unit 13 for evaluating each test pulse width regard to that stimulation response. According to a preferred embodiment, the stimulation response data is obtained from ECAPs measurements carried out by the CI device 10, with the evoked potential data being recorded by reverse telemetry from the ICS 14 to the sound processing subsystem 11, from where the data is supplied via the programming interface 15 to the programming unit 13 (this path is schematically indicated at 58 in FIG. 4).

Figure 8:
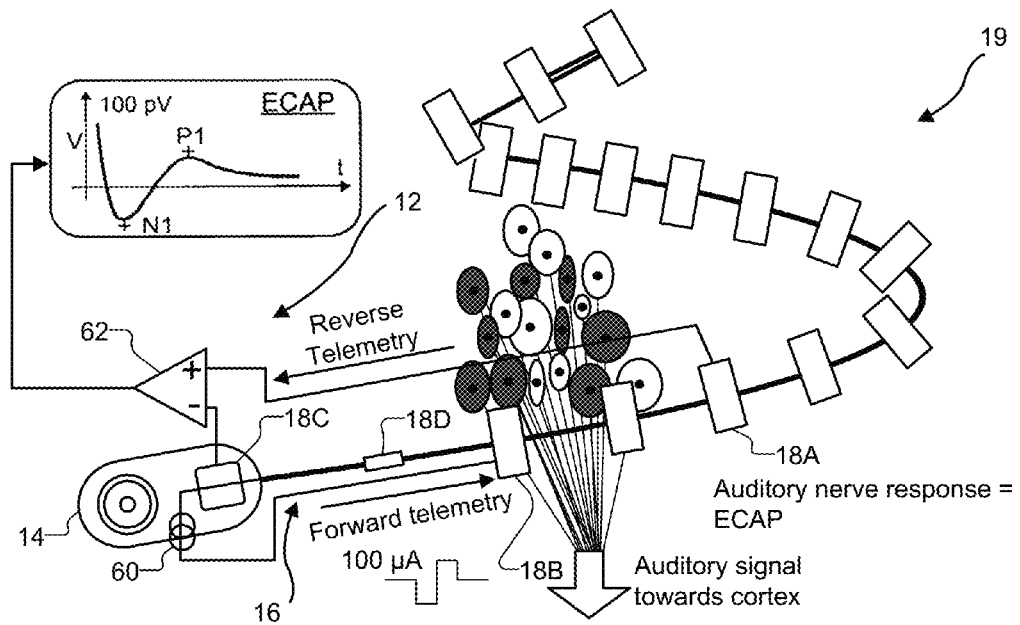
FIG. 8 is a schematic illustration of a setup for ECAP-measurements by reverse telemetry.

FIG. 8 shows a schematic illustration of an example of auditory nerve excitation and the resulting ECAP recording at electrode 18A by reverse telemetry, following electrical stimulation at electrode 18B by forward telemetry (the stimulated neurons are indicated by dark grey circles in FIG. 8, the return electrodes are indicated at 18C and 18D, respectively). The current-source 60 and the amplifiers 62 are positioned inside the receiver part of the ICS 14. The typical ECAP peaks are indicated at N1 and P1 in example of an ECAP signal vs. time in FIG. 8. The peaks may be used as markers to measure the ECAP amplitude as the differential voltage between P1 and N1.

Alternatively, stimulation response data may be obtained by a scalp recording electrode or any other known means of recording neural responses. In particular, stimulation response data may be obtained from auditory brain stem response (ABR) measurements, electrically evoked stapedius reflex measurements, post-auricular muscle reflex measurements, cortical potential measurements or iris contraction measurements. According to further alternative embodiments, the stimulation response data may be obtained from EEG (electro-encephalography), MEG (magneto-encephalography) or functional imaging measurements. According to a still further embodiment, stimulation response data may be obtained from psychophysical measurements, such as detection threshold measurements or loudness ratings, which, however, involve active participation of the patient, limiting this approach in practice to adult patients only.

According to one example, which is schematically shown in FIG. 5, for each test shape parameter set a minimum amplitude scaling factor required to evoke a given response is obtained from the response measurement. Typically, the given neural response will be a neural response threshold. Rather than directly measuring the response, an indirect estimate or a related measure thereof, such as tNRI (neural response imaging) levels derived from ECAPs measurements (cf., for example "Comparisons between neural response imaging thresholds, electrically evoked auditory reflex thresholds and most comfortable loudness levels in CII bionic ear users with HiResolution sound processing strategies", by D. M. Han et al., in Acta Otolaryngol 125(7), 2005, p. 732-735) may be determined.

The investigated test shape parameter sets then may be scored and ranked according to the power consumption required for generating the respective test pulse. According to a more elaborate scoring scheme, in addition a cost function could be used which incorporates additional penalties for various undesirable properties of the pulse shape, such as stimulation near the compliance voltage of the implant, or excessive total pulse duration.

Preferably, the test shape parameter sets are iteratively evaluated in subsequent groups, wherein the optimal test shape parameter set, i.e., the parameter set having been awarded the best evaluation across all groups, is finally used for programming the CI device 10. According to such iterative method, a first group of n test parameter sets is investigated, and after investigation of the first group a second group of n parameter sets is defined based on the scoring results obtained for the first group of parameter sets, the second group is investigated, and so on, until a stopping criterion is reached. Such stopping criterion may be the lapse of a given time period since the start of the optimization procedure, or the iteration may be stopped when for a given time period no test shape parameter set has been found having a better evaluation than the already evaluated test shape parameter sets.

One benefit of group-wise iteration is that it thereby may be avoided that the optimization process halts prematurely after having reached a particular local maximum of the scoring function.

An alternative optimization procedure is illustrated in FIG. 6, wherein the test shape parameter sets are provided such that each test shape parameter set results in the same predetermined power consumption of the respective test pulse. In this case the test shape parameter sets are scored according to the magnitude of the stimulation response level, i.e. the parameter set resulting in the highest stimulation response level will receive the highest score.

While in the example of FIG. 5, the measuring system has to return threshold stimulus amplitudes, it has to return response amplitudes in the example of FIG. 6. A priori, one may expect that the procedure of FIG. 5 is slower than the procedure of FIG. 6 on each iteration cycle, since the determination of a response threshold requires taking repeated measurements at various stimulus amplitudes. However, the procedure of FIG. 6 may be prone to greater intrinsic variability due to the fact that stimulation is not targeted at a constant criterion response level as in the procedure of FIG. 5.

In any case, the optimization procedure serves to determine the optimal pulse shape parameter set which is to be stored in the memory 56 for operation of the CI device 10.

Preferably, the optimal test shape parameter set is determined for each stimulation channel separately, with test pulses being applied only to one stimulation channel at a time. In general, the CI device 10 may be designed for electrical stimulation of the cochlea only, for stimulation of the cochlea with light, for the stimulation of the cochlea with heat, or combinations of such stimuli.

By optimizing the stimulation pulse shape, the present invention helps to reduce power consumption of the implant, thereby prolonging battery life and/or allowing for smaller speech processor designs. This is important in view of the fact that size and weight of external components are major criteria for the comfort, usability and esthetic appeal of a CI device to a patient.

What is claimed is:
1. A system comprising a device for neural stimulation of a cochlea of a patient, means for in-situ measuring a stimulation response of the patient to the neural stimulation of the cochlea, and a programming unit for adjusting the stimulation device;
   the stimulation device comprising
      a stimulation signal unit adapted to generate a stimulation signal for each stimulation channel included in a plurality of stimulation channels, the stimulation signal including pulses having a shape determined by a shape parameter set including at least one shape parameter;
      a cochlear implant stimulation arrangement comprising the plurality of stimulation channels and configured to stimulate the cochlea according to the stimulation signal;
   the measuring means being adapted to provide, to the programming unit, patient-specific response data concerning the stimulation response,
   the programming unit being adapted to control the stimulation signal unit by
      subsequently supplying a plurality of different test shape parameter sets to the stimulation signal unit and thereby causing the stimulation signal unit to generate a plurality of test pulses that each correspond to a different test shape parameter set included in the plurality of test shape parameter sets,
      evaluating each test shape parameter set included in the plurality of test shape parameter sets according to the respective stimulation response data supplied by the measuring means and according to a power consumption of the plurality of test pulses generated according to the respective test shape parameter sets,
      determining an optimal test shape parameter set included in the plurality of test shape parameter sets and that has a lowest power consumption per test pulse for a given stimulation response to a test pulse generated according to the optimal test shape parameter set, and programming the stimulation device based on the optimal test shape parameter set.

2. The system of claim 1, wherein the cochlear implant stimulation arrangement comprises a plurality of electrodes for electrical stimulation of the cochlea.

3. The system of claim 1 wherein the programming unit is adapted to determine the optimal test shape parameter set for each stimulation channel separately.

4. The system of claim 3, wherein the programming unit is adapted to cause the stimulation unit to apply test pulses only to one stimulation channel at a time.

5. The system of claim 1, wherein the programming unit is adapted to stop the search for the optimal test shape parameter set after a given time period has lapsed since the start of the search.

6. The system of claim 1, wherein the programming unit is adapted to stop the search for the optimal test shape parameter set when for given time period no test shape parameter set has been found having a better evaluation than the already evaluated test shape parameter sets.

7. The system of claim 1, wherein the programming unit is adapted to obtain for each test shape parameter set an amplitude scaling factor required to evoke a predetermined response by the patient, the programming unit being further adapted to use the amplitude scaling factor for evaluating the power consumption of the respective test pulse.

8. The system of claim 7, wherein the predetermined response is a threshold level.

9. The system of claim 1, wherein the programming unit is adapted to provide the test shape parameter sets such that each test shape parameter set results in the same predetermined power consumption of the respective test pulse, the programming unit being further adapted to select that test shape parameter set as the optimal test shape parameter set which results in the largest stimulation response level.

10. The system of claim 1, wherein the programming unit is adapted to supply and evaluate the test shape parameter sets in subsequent groups, wherein for each group an optimal test shape parameter set is determined, wherein the test shape parameter sets of each group are selected according to the evaluation result of the previous group test shape parameter sets, and wherein that optimal test shape parameter set is selected for programming of the stimulation device which has the best evaluation.

11. The system of claim 1, wherein the stimulation device comprises means for providing an input audio signal and a sound processor for generating a neural stimulation signal from the input audio signal, with the sound processor comprising the stimulation signal unit.

12. The system of claim 1, wherein the measuring means is adapted to measure electrically-evoked compound action potentials (ECAPs) and base the patient-specific response data on the measured ECAPs.

13. The system of claim 12, wherein the measuring means comprises the stimulation electrodes, the measuring means being adapted to transmit the response data via a reverse telemetry link to the sound processor.

14. The system of claim 1, wherein the measuring means is adapted to measure auditory brain stem responses (ABRs) and base the patient-specific response data on the measured ABRs.

15. The system of claim 1, wherein the measuring means is adapted to provide the patient-specific response data from electrically evoked stapedius reflex, post-auricular muscle reflex, cortical potentials or iris contraction measurements.

16. The system of claim 1, wherein the measuring means is adapted to measure electro-encephalography (EEG) responses, magneto-encephalography (MEG) responses, or functional imaging measurements and base the patient-specific response data on the EEG responses, MEG responses, or functional imaging measurements.

17. The system of claim 1, wherein the measuring means is adapted to perform psychophysical measurements and base the patient-specific response data on the psychophysical measurements.

18. The system of claim 1, wherein the pulses are staircase pulses, a sum of exponentials pulses or a sum of Gaussians pulses.

19. The system of claim 1, wherein the stimulation signal unit is for generating biphasic pulses.

20. The system of claim 1, wherein the programming unit is implemented by a PC communicating with the stimulation device via a programming interface.

21. A method of individually adjusting a device for neural stimulation of a cochlea of a patient, comprising:

generating, by a stimulation signal unit, a test stimulation signal, the test stimulation signal including pulses having a test shape determined by a test shape parameter set including at least one shape parameter;

supplying the stimulation signal to a cochlear implant arrangement comprising a plurality of stimulation channels for stimulating the cochlea according to the test stimulation signal;

obtaining patient-specific response data concerning the stimulation response to the test stimulation signal by in-situ measuring a response of the patient to the stimulation of the cochlea;

repeating the preceding steps with different test shape parameter sets;

evaluating each test shape parameter set according to the respective stimulation response data and according to a power consumption of the pulse generated according to the respective test shape parameter set;

determining an optimal test shape parameter set having a lowest power consumption per pulse for a given stimulation response to a pulse generated according to that test shape parameter set; and programming the stimulation device based on the optimal test shape parameter set.

22. The method of claim 21, wherein the optimal test shape parameter set is determined for each stimulation channel separately.

23. The method of claim 21, wherein test pulses are applied only to one stimulation channel at a time.

* * * * *